United States Patent [19]

Sunmo

[11] Patent Number: 5,318,581
[45] Date of Patent: Jun. 7, 1994

[54] AID TO MAKING HOLES

[76] Inventor: Leif Sunmo, Kvarngränd 3, S-432 34 Varberg, Sweden

[21] Appl. No.: 859,355
[22] PCT Filed: Dec. 7, 1990
[86] PCT No.: PCT/SE90/00810
 § 371 Date: May 18, 1992
 § 102(e) Date: May 18, 1992
[87] PCT Pub. No.: WO91/08712
 PCT Pub. Date: Jun. 27, 1991

[30] Foreign Application Priority Data

Dec. 8, 1989 [SE] Sweden .................. 8904141

[51] Int. Cl.⁵ .......................................... A61B 17/34
[52] U.S. Cl. .................. 606/185; 606/184; 606/167; 606/181
[58] Field of Search .............. 30/366; 83/866; 604/115, 117, 158, 162, 171, 263; 606/167, 172, 181, 182, 183, 184, 185, 188, 189

[56] References Cited

U.S. PATENT DOCUMENTS

| 4,883,068 | 11/1989 | Dechow | 604/117 |
| 4,889,117 | 12/1989 | Stevens | 606/185 |
| 4,935,013 | 6/1990 | Haber et al. | 604/263 |
| 4,943,281 | 7/1990 | Kothe | 604/192 |

Primary Examiner—John D. Yasko
Assistant Examiner—N. Kent Gring
Attorney, Agent, or Firm—Dvorak and Traub

[57] ABSTRACT

An aid to making holes for the purpose of puncturing of parts of the body, comprising a hole-maker capable of being guided by a guide component. A hole-maker is connected to an articulated link with a to-and-fro pliable effect attached to the guide component. The simple function and manufacture of the aid in question are achieved thanks to the present invention.

7 Claims, 3 Drawing Sheets

AID TO MAKING HOLES

The present invention relates to an aid to making holes for the purpose of puncturing of parts of the body, and comprises a hole-maker capable of being guided by a guide component.

Previously disclosed aids of the aforementioned kind, for example the arrangement in accordance with SE, B, 8003057-0 (Publ. No. 422 150), do not permit a safe and simple function in line with current requirements.

The principal object of the present invention is thus, in the first place, to make available an aid to making holes in parts of the body, which solves said problem by simple means with regard both to the manufacture and use of the aid.

Said object is achieved by means of an aid in accordance with the present invention, which is characterized essentially in that the hole-maker is connected to a pliable link capable of to-and-fro movement attached to the guide component.

The invention is described below as a preferred illustrative embodiment with reference to the drawings, in which.

Figure 1:
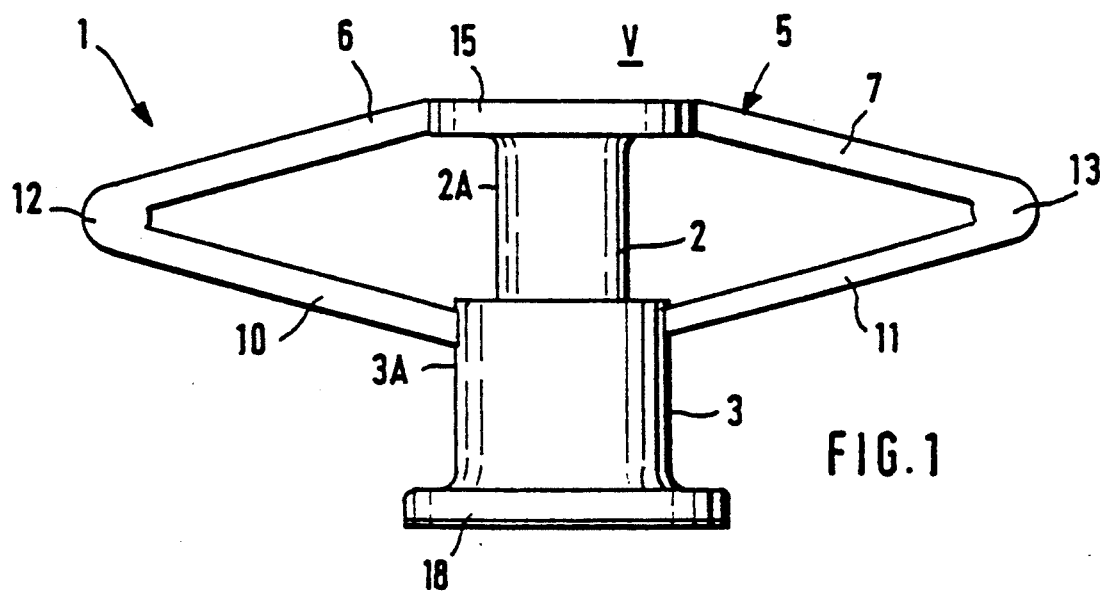
FIG. 1 shows a side-view of an aid to making holes in the position of rest.

An aid to making holes 1 arranged in accordance with the present invention, comprising a hole-maker 2 which is guided by a guide component 3 so as to permit the puncturing of parts of the body, for example when pricking a finger 4 in conjunction with taking a blood sample, etc., has the hole-maker 2 attached to the guide component 3 via a link 5. Said link, which can be in the form of a number of pivotally arranged arms 6, 7, is pliably connected to the guide component 3 in a manner capable of to-and-fro movement in the direction of the arrows 8, 9, against the effect of an influencing force which acts contrary to the directions referred to above.

Said arms 6, 7 are preferably arranged in pairs, or in some other desired number, with each being supported on a corresponding counter-pressure component 10, 11 attached to the guide component 3 of the hole-maker and preferably projecting laterally outwards from said preferably sleeve-shaped guide component 3 of the hole-maker.

For example, said counter-pressure components may be in the form of so-called counter-pressure arms 10, 11 which are appropriately integrated with the sleeve-shaped guide component 3 of the hole-maker at its rear end 3A, viewed in the direction of use 8, i.e. the direction of penetration, or are attached in some other appropriate fashion to said component 3. A hinge 12, 13 is arranged so that it is supported preferably at the outer ends 10A, 11A of each of said counter-pressure arms 10, 11. Connected to each hinge 12, 13 is one of said articulated connecting arms 6, 7, which runs in a lateral sense across the direction of use 8 of the aid inwards towards a compression component 15 situated preferably centrally at the middle 14 of the aid. Said compression component may appropriately be in the form of a thumb-pressure pad 15, which is integrated with said articulated connecting arm/arms 6,7 and which consists preferably of the rear end of a casing body 16 for the hole-maker 2 situated centrally on the aid 1 in question.

Said hole-maker 2 may, as can be appreciated from the example shown here, consist of different materials, in conjunction with which the body 16 itself may be made of extruded plastic, for example, whereas the actual tip may be in the form of a metal needle 17, which is fixed to the body 16 by its rear end 17A. By positioning the needle 17, it is possible to ensure its location in precisely the desired position, so that the correct depth by which the needle projects can be guaranteed in every case. The needle is thus not able to penetrate too deeply into a finger, for example, which has been one of the disadvantages of previously disclosed hole-makers.

Otherwise the hole-making aid 1 also consists of a plastic material, although the use of other materials, such as metallic materials, for example, may be considered.

Figure 2:
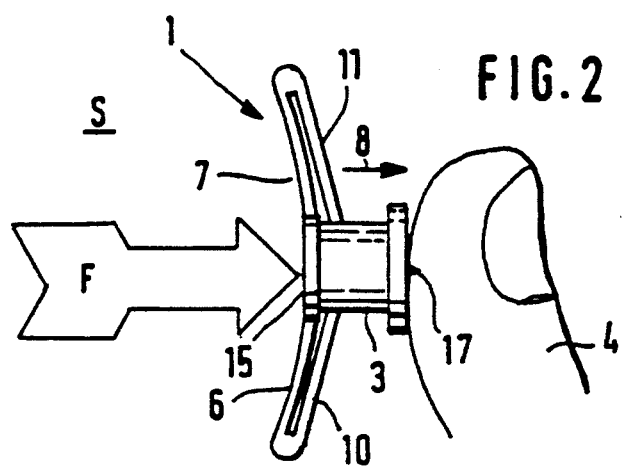
FIG. 2 shows an aid to making holes in the penetration position.
Figure 3:
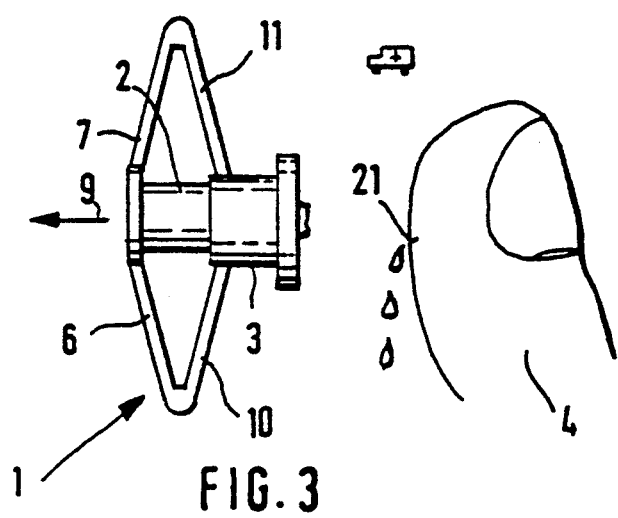
FIG. 3 shows said aid to making holes after making a hole.

Thanks to the characteristics of the material, the articulated connecting arms 6, 7 and the counter-pressure arms 10, 11 can be so arranged as to exhibit a spring action in relation to one another, so that the articulated connecting arms 6, 7 are caused to spring back in the direction of the arrow 9, after having been pushed down in the direction of the arrow 8, once the thumb has been pressed against the thumb-pressure pad 15. The hinges 12. 13 can also be arranged with spring action in a similar way to that described above, so as to cause the connecting arms 6, 7 to spring back after these have been pushed down with a certain force F, as shown in FIGS. 2 and 3 in the drawings.

The connecting arms 6, 7 and the counter-pressure arms 10, 11 can be attached to one another via hinges 12, 13 with the pressure pad 15 and the guide component 3 between them, so that an acute angle X is formed at each hinge 12, 13 between the arms 6–7; 10–11, viewed from the side looking at the aid 1, when the aid 1 is held with its hole-maker 2 in the retracted position of rest V ready for making holes, like a rhombus or the arms of a manually operated jack. In the so-called penetration position S, as illustrated in the drawings in FIG. 2, the arms 6, 7 are moved against spring pressure inwards towards the arms 10, 11 until they come close to one another in pairs 6, 10; 7, 11 after the pressure pad 15 has been caused by a thumb to press the hole-maker 2, preferably exhibiting cylindrical cross-section, with a certain force F into the guide sleeve 3 which, at its front end 3B, which is designed to be capable of being turned to face a finger 4 or some other intended part of the body before a hole is made therein, exhibits a flared contact component 18, for example a ring, which provides support for the aid during the hole-making operation.

Figure 4:
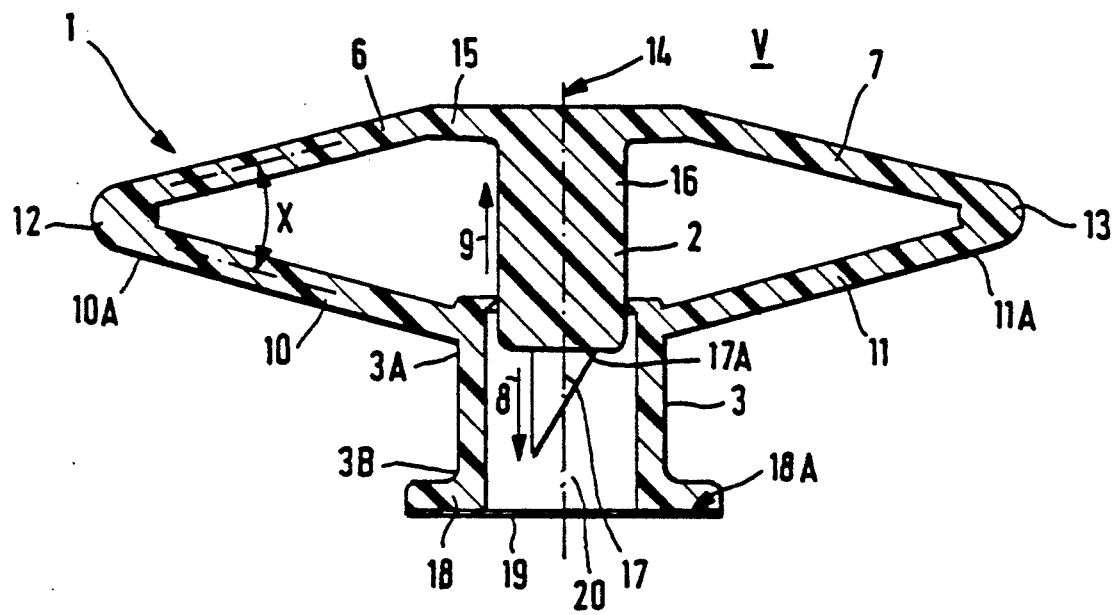
FIG. 4 shows a cross-section through an aid to making holes in the position of rest.
Figure 5:
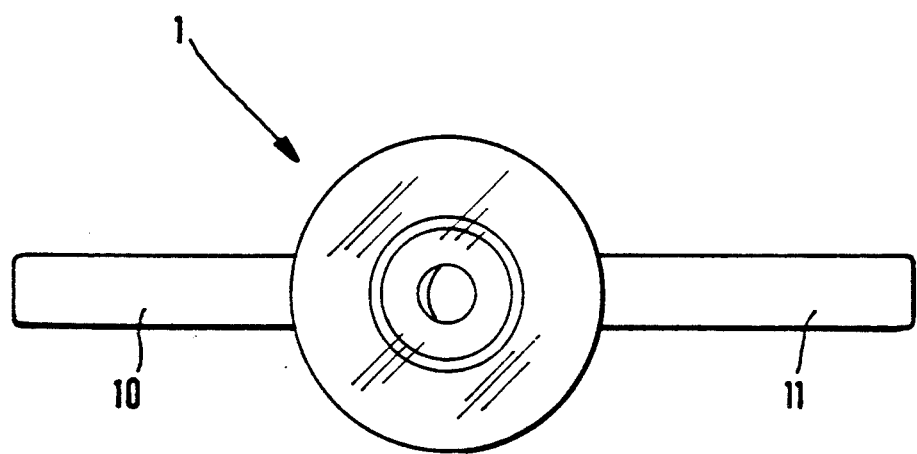
FIG. 5 shows a front view of the aid to making holes.
Figure 6:
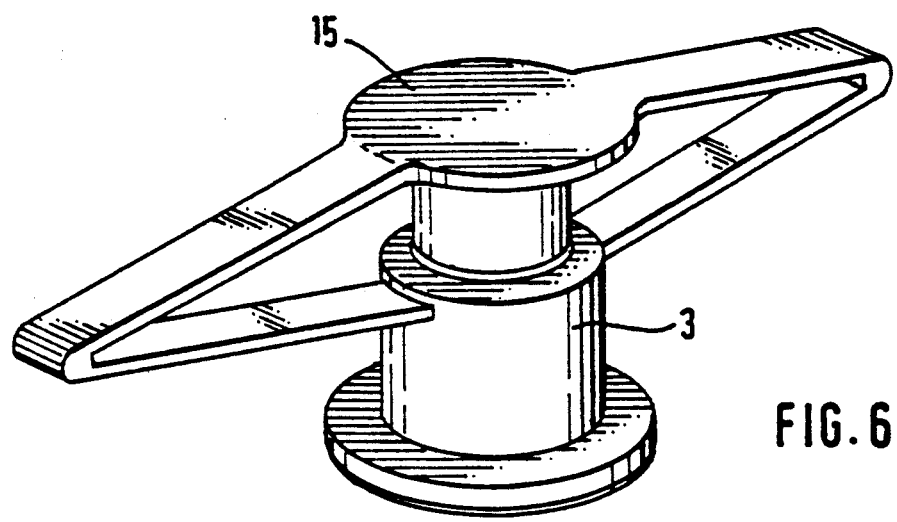
FIG. 6 shows a perspective view of the aid in the position of rest.
Figure 7:
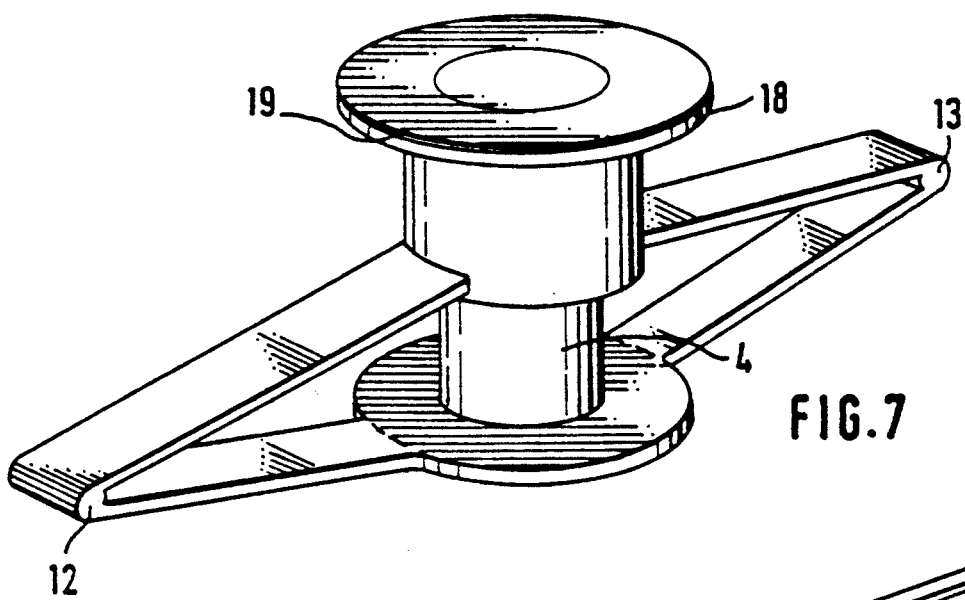
FIG. 7 shows a perspective view of the aid in the position of rest, viewed from below.
Figure 8:
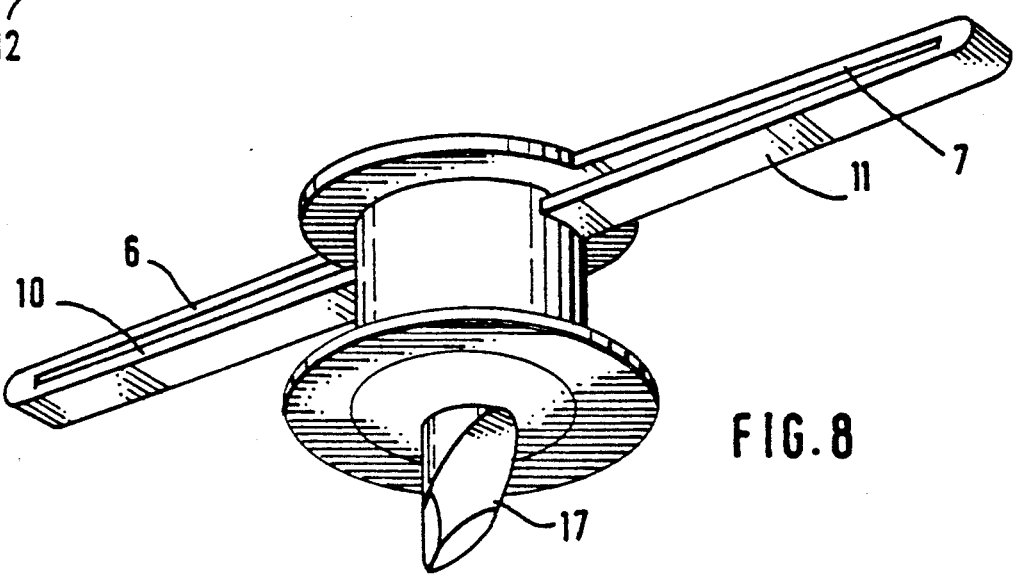
FIG. 8 shows the aid, viewed from below and in the penetration position.

In order to protect the nail 17, etc., a degradable cover 19 is arranged on said contact component 18, so that the needle 17 cannot be contaminated before use. The effective sharp point 17 of the hole-maker, for example a needle, is so arranged as to be accommodated internally within the accommodating space 20 of said guide component 3 when the hole-maker is being held in the position of rest V, before or after the hole-making operation (FIG. 4 and FIG. 3). The cover 19, which can consist of a membrane of a plastic material or similar, and which is capable of being acted upon by the hole-maker from the inside for the purposes of its degradation, in such a way that the sharp point 17 can be caused to project for hole-making. A piece of plastic film may be welded or bonded, for example, to the outside 18A of the contact component 18.

After the hole-making operation the sharp point 17 is withdrawn, thanks to the spring function of the aid, back into the space 20, when the sharp point 17 is protected against contact. Any disease, such as yellow jaundice or HIV, etc., which may have been transferred from the body 4 to the sharp point 17 during the hole-making operation is prevented by the function and construction of the aid from being spread further via the aid 1, through accidental contact with it, which is of the disposable type, of course.

The function and construction of the aid 1 should have been appreciated clearly from the foregoing and the drawings shown here, although it can be stated briefly that, when the aid 1 is held against a part of the body 4 and pressure is applied against the pressure pad 15, for example with the thumb, at the same time as the index finger and the middle finger, for example, are appropriately placed against the arms 10, 11, the sharp point 17 is pushed out in the direction of the arrow 8, so that the part of the body 4 concerned is punctured, as shown in FIG. 2 in the drawings.

As the aid 1 is removed from the hole 21 which has been produced, the sharp point 17 is automatically retracted into the aid, where it is well protected inside the guide component 3 behind the remains of the degraded protective membrane 19, and within the limits of the guide component 3. The aid 1 is thus both simple to manufacture in hygienic materials and by the use of simple processes, and is easy and safe to use, including by persons who are not familiar with it. The invention is not restricted to the illustrative embodiments described above and shown in the drawings, however, but can be modified within the scope of the Patent claims without departing from the idea of invention.

The number of arms can be varied, for example, as can their form and that of the aid in question.

I claim:

1. An aid for puncturing a part of a body comprising:
    a hole-maker movably disposed in a sleeve-shaped guide component;
    a pair of counter-pressure arms connected to one end of said sleeve-shaped guide component and projecting laterally and upwardly above said sleeve-shaped guide component;
    said hole-maker having at one end a pressure plate provided with a pair of laterally projecting articulated arms coextensive with said counter-pressure arms and defining therebetween hinges, a free end of the hole-maker being provided with a sharp point and protectively positioned within said sleeve-shaped guide component, all of said arms being flexible to permit movement of said hole-maker to expose its sharp point out of the confines of said sleeve-shaped guide component upon application of force on the pressure component, said articulated arms and said counter-pressure arms exhibiting a spring action therebetween to withdraw said sharp point into said sleeve-shaped guide component upon removal of said force, the articulated arms and the counter-pressure arms are connected to one another and to the pressure plate and to the guide component in such a way that all of the arms form acute angles between themselves at each hinge when the aid is held with its hole-maker in the retracted position of rest ready for making holes.

2. An aid to making holes in accordance with claim 1, in which the point of the hole-maker preferably consists of a metal material while the rest of the aid consists of plastic material, characterized in that said guide component sleeve is designed to accommodate and guide the hole-maker at the other end which is capable of being turned to face an object in which it is intended to make a hole, said guide component sleeve having a contact component.

3. An aid to making holes in accordance with claim 1, characterized in that the sharp point of the hole-maker is so arranged as to be accommodated internally within said guide component sleeve when the hole-maker is being held in the position of rest.

4. An aid to making holes in accordance with claim 1, in which the sharp point preferably consists of a metal material while the rest of the aid consists of plastic material, characterized in that a guide component sleeve is designed to accommodate and guide the hole-maker at its end which is capable of being turned to face an object in which it is intended to make a hole exhibits a contact component.

5. An aid to making holes in accordance with claim 1, characterized in that the aid to making holes exhibits on a front face a degradable protective cover capable of being acted upon by the hole-maker, in conjunction with which the cover consists of a membrane.

6. An aid for puncturing a part of a body comprising:
    a hole-maker movably disposed in a sleeve-shaped guide component;
    a pair of counter-pressure arms connected to one end of said sleeve-shaped guide component and projecting laterally and upwardly above said sleeve-shaped guide component;
    said hole-maker having at one end a pressure plate provided with a pair of laterally projecting articulated arms coextensive with said counter-pressure arms and defining therebetween hinges, a free ned of the hole-maker being provided with a sharp point and protectively positioned within said sleeve-shaped guide component, all of said arms being flexible to permit movement of said hole-maker to expose its sharp point out of the confines of said sleeve-shaped guide component upon application of force on the pressure component, said articulated arms and said counter-pressure arms exhibiting a spring action therebetween to withdraw said sharp point into said sleeve-shaped guide component upon removal of said force; and
    a degradable protective cover disposed on a font face of the aid for puncturing a part of a body wherein the degradable protective cover is capable of being acted upon by the hole-maker, in conjunction with which the cover consists of a membrane.

7. An aid for puncturing a part of a body comprising:
    a hole-maker movably disposed in a sleeve-shaped guide component;
    a pair of counter-pressure arms connected to one end of said sleeve-shaped guide component and projecting laterally and upwardly above said sleeve-shaped guide component;

said hole-maker having at one end a pressure plate provided with a pair of laterally projecting articulated arms coextensive with said counter-pressure arms and defining therebetween hinges, a free ned of the hole-maker being provided with a sharp point and protectively positioned within said sleeve-shaped guide component, all of said arms being flexible to permit movement of said hole-maker to expose its sharp point out of the confines of said sleeve-shaped guide component upon application of force on the pressure component, said articulated arms and said counter-pressure arms exhibiting a spring action therebetween to withdraw said sharp point into said sleeve-shaped guide component upon removal of said force; and a degradable protective cover disposed on a second end of said guide component sleeve wherein the degradable protective cover is capable of being acted upon by the hole-maker, in conjunction with which the cover consists of a membrane.

* * * * *